United States Patent
Keyghobad et al.

(10) Patent No.: US 10,928,352 B2
(45) Date of Patent: Feb. 23, 2021

(54) ANALYTE DETECTION IN A CONTAMINATED SAMPLE

(71) Applicant: NANOBIO SYSTEMS INC., Marblehead, MA (US)

(72) Inventors: Seyamak Keyghobad, Marion, MA (US); Michael Bruckman, Rocky River, OH (US); Eve F. Fabrizio, Avon, OH (US); Bindi Patel, Westlake, OH (US)

(*) Notice: Subject to any disclaimer, the term of this patent is extended or adjusted under 35 U.S.C. 154(b) by 0 days.

(21) Appl. No.: 16/760,720

(22) PCT Filed: Oct. 30, 2018

(86) PCT No.: PCT/US2018/058149
§ 371 (c)(1),
(2) Date: Apr. 30, 2020

(87) PCT Pub. No.: WO2019/089546
PCT Pub. Date: May 9, 2019

(65) Prior Publication Data
US 2020/0333281 A1    Oct. 22, 2020

Related U.S. Application Data

(60) Provisional application No. 62/579,312, filed on Oct. 31, 2017.

(51) Int. Cl.
*G01N 27/327* (2006.01)
*C12Q 1/00* (2006.01)
*A61B 5/145* (2006.01)

(52) U.S. Cl.
CPC ..... *G01N 27/3274* (2013.01); *A61B 5/14532* (2013.01); *C12Q 1/006* (2013.01); *G01N 27/3272* (2013.01); *G01N 27/3273* (2013.01)

(58) Field of Classification Search
None
See application file for complete search history.

(56) References Cited

U.S. PATENT DOCUMENTS

| | | |
|---|---|---|
| 6,560,471 B1 | 5/2003 | Heller |
| 2003/0088166 A1 | 5/2003 | Say |
| 2007/0066873 A1 | 3/2007 | Kamath |
| 2012/0283538 A1 | 11/2012 | Rose |
| 2014/0197042 A1 | 7/2014 | Zhang et al. |
| 2017/0281092 A1 | 10/2017 | Burnette et al. |

OTHER PUBLICATIONS

International Search Report and Written Opinion dated Jan. 11, 2019 for Application No. PCT/US2018/058149.

*Primary Examiner* — J. Christopher Ball
(74) *Attorney, Agent, or Firm* — Tarolli, Sundheim, Covell & Tummino LLP

(57) ABSTRACT

A system can facilitate detection of the presence of an analyte or a contaminant in a contaminated sample. The system includes a first sensor to detect the analyte and a contaminant in the sample and a second sensor to detect the analyte or the contaminant in the sample. The detections are compared by a device comprising a processor to eliminate either the analyte or the contaminant from the final detected result.

5 Claims, 17 Drawing Sheets

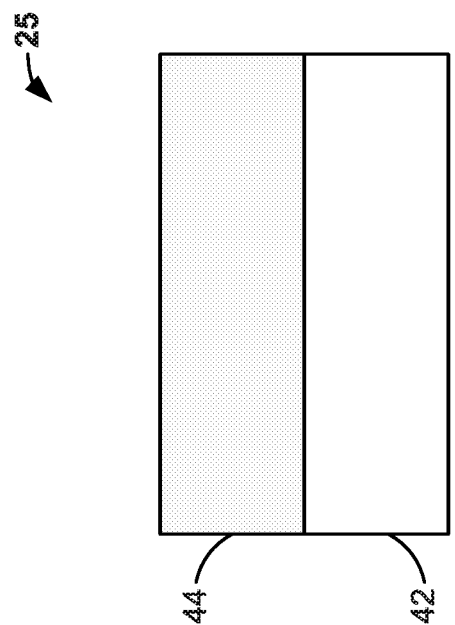
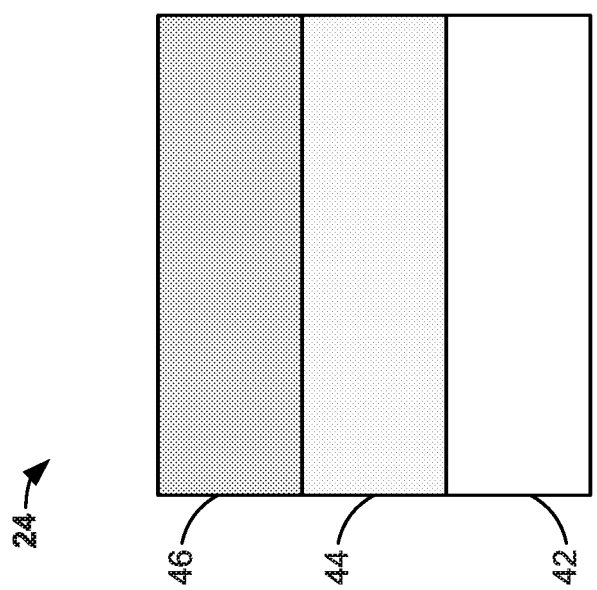
FIG. 4

ANALYTE DETECTION IN A CONTAMINATED SAMPLE

RELATED APPLICATIONS

This application is a national stage entry of PCT Appl. No. PCT/US18/58149, filed Oct. 30, 2018, entitled "ANALYTE DETECTION IN A CONTAMINATED SAMPLE", which claims the benefit of U.S. Provisional Application No. 62/579,312, filed 31 Oct. 2017, entitled "ANALYTE DETECTION IN A CONTAMINATED SAMPLE". This provisional application is hereby incorporated by reference in its entirety for all purposes.

TECHNICAL FIELD

The present disclosure relates generally to testing for analyte concentration in a sample, and, more specifically, to systems, apparatuses, and methods that facilitate detecting the analyte in a contaminated sample.

BACKGROUND

Determining the concentration of an analyte (e.g., glucose, cholesterol, lactate, or the like) in a sample is important for diagnosis and management of different health conditions. The analyte can be found in differing concentrations in many biofluids, including blood, interstitial fluid, urine, sweat and saliva. Often, the presence of analytes in a sample can be detected by sensors using an indirect mechanism. In other words, the analyte interacts with a portion of the sensor, which produces an effect that is measurable by another portion of the sensor. Generally, the measured effect reflects the concentration of the analyte in the sample. However, when the sample is contaminated, contaminants can also be measurable by the other portion of the sensor. Accordingly, the concentration of the analyte determined in a contaminated sample may not reflect the actual concentration of the analyte in the sample.

SUMMARY

The present disclosure relates generally testing for analyte concentration in a sample and, more specifically, to systems, apparatuses, and methods that facilitate detecting the analyte concentration in a contaminated sample.

In one aspect, the present disclosure can include a system to detect the presence of an analyte in a contaminated sample. The system can include a first sensor, a second sensor, and a processing device. The first sensor can include a first electrode and one or more first layers atop the first electrode to detect the analyte and the contaminant in the sample. The second sensor can include a second electrode and one or more second layers atop the second electrode to detect the analyte or the contaminant in the sample. The processing device can include a processor to receive a first signal from the first sensor related to the detection of the analyte and the contaminant; receive a second signal from the second sensor related to the detection of the analyte or the contaminant; and determine a concentration of the analyte or the contaminant by comparing the first signal and the second signal.

In another aspect, the present disclosure can include another system to detect the presence of glucose in a saliva sample contaminated by hydrogen peroxide. The system can include a first sensor, a second sensor, and a processing device. The first sensor can include a first electrode; a base layer on the first electrode comprising carbon nanotubes to detect hydrogen peroxide in a saliva sample; a middle layer on the base layer comprising chitosan; and a top layer on the middle layer to detect glucose in the saliva sample, comprising glucose oxidase and gold nanoparticles that binds to the chitosan of the middle layer. The second sensor can include a second electrode and at least one layer to detect hydrogen peroxide in the saliva sample. The processing device can include a processor to: receive a first signal from the first sensor indicating the detected glucose and hydrogen peroxide; receive a second signal from the second sensor indicating the detected hydrogen peroxide; and determine a concentration of the glucose in the saliva sample by taking the absolute value of the second signal subtracted from the first signal.

In another aspect, the present disclosure can include a method for detecting the presence of an analyte in a contaminated sample. The method can be executed by a system comprising a processor. Steps of the method include receiving a first signal from a first sensor related to a detection of an analyte and a contaminant in a sample; receiving a second signal from a second sensor related to a detection of the analyte or the contaminant in the sample; and determining a concentration of the analyte or the contaminant by comparing the first signal and the second signal.

In a further aspect, the present disclosure can include an apparatus for detecting the presence of an analyte in a contaminated sample. The apparatus can include a first sensor comprising a first electrode and one or more first layers atop the first electrode to detect an analyte and a contaminant in a sample. The apparatus can also include a second sensor comprising a second electrode and one or more second layers atop the second electrode to detect the analyte or the contaminant in the sample. The apparatus can also include a third sensor to detect environmental data. The first sensor, the second sensor, and the third sensor can be arranged in an array.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 4 is a block diagram showing a configuration of layers that can be used in the sensors shown in FIGS. 2 and 3;

DETAILED DESCRIPTION

I. Definitions

Figure 1:
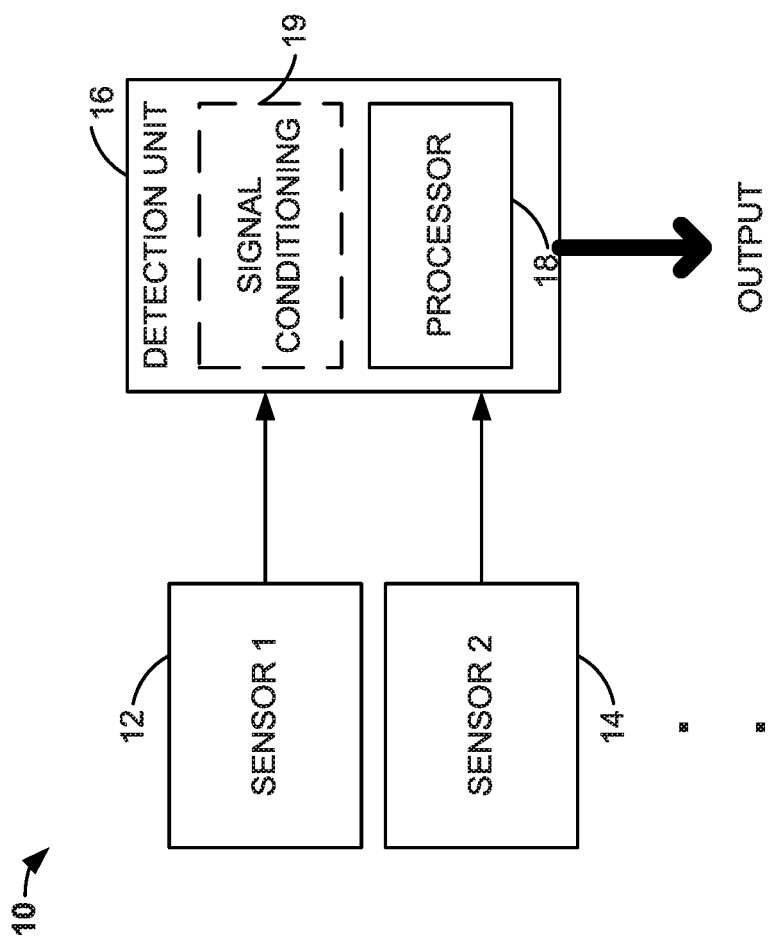
FIG. 1 is a block diagram showing an example of a system to detect the presence of an analyte in a contaminated sample according to an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "sensor" refers to a device that detects or measures a physical property and records, indicates, or otherwise responds to the measured physical property. The sensor can determine the presence of an analyte in a sample either directly or indirectly (through detecting a secondary effect of the analyte).

As used herein, determining the presence of the analyte "directly" can refer to the detection of the analyte by a transducer, which can transform the detected analyte into a measurable signal that can be related to the presence of the analyte.

As used herein, determining the presence of the analyte "indirectly" can refer to the detection of an effect that reflects the analyte. For example, the sensor can include a recognition component that interacts (e.g., binds, reacts, or the like) with the analyte in the sample to produce an effect measurable by a transducer, which can transform the effect into a measurable signal that can be related to the presence of the analyte in the sample. The recognition component can employ biomolecules (e.g., as tissue, microorganisms, organelles, cell receptors, enzymes, antibodies, nucleic acids, or the like) to interact with the analyte.

As used herein, the term "sample" refers to a volume of a specimen (e.g., a fluid, colloid, suspension, etc.) taken for testing or analysis. The sample can include one or more contaminants and one or more analytes. For example, the sample can include a biofluid, like saliva, sweat, tears, interstitial fluid, blood, urine, or the like. In some instances, the sample can be processed, diluted, or the like.

As used herein, the term "analyte" refers to a substance whose chemical constituents are being identified and measured. Example analytes include glucose, cholesterol, lactate, and the like.

As used herein, the term "contaminant" refers to any substance that makes a sample impure for analyte detection. The contaminant can be, for example, a reactive oxygen species, an enzymatic by-product, or the like.

As used herein, the term "environmental data" refers to measurements related to factors present in external surroundings of the sensor, including temperature, humidity, pressure, and the like.

As used herein, the term "sample condition data" refers to measurements related to factors present in the sample other than the analyte and contaminant. Examples of sample condition data include pH, ionic strength, bacterial load, microorganism load, oxygen content, protein content, reducing agents, etc.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to testing for analyte concentration in a sample. Sweat, saliva, tears, interstitial fluid, blood, urine, as well as many other potential samples, can include concentrations of the analyte. However, these samples also can include contaminants that can interfere with the detection of the analyte (affecting sensitivity, selectivity, and/or measurement repeatability), making the detection of the analyte in these samples not only impractical, but potentially inaccurate. Accordingly, the present disclosure relates, more specifically, to systems, apparatuses, and methods that facilitate detecting the analyte concentration in a contaminated sample.

While previous analyte sensors only include a single analyte-sensitive sensor, the present disclosure sets forth an analyte detection device that includes at least two sensors. The at least two sensors can include a sensor that is sensitive to the analyte and the contaminant and another sensor that is sensitive to the contaminant alone. A device comprising a processor can receive signals from each sensor and determine the concentration of the analyte based on the comparison.

III. Systems

One aspect of the present disclosure can include a system 10 (FIG. 1) that can detect the presence of one or more analytes in a sample that also includes one or more contaminants (e.g., reactive oxygen species, enzymatic byproducts, etc.). The sample can be a fluid, colloid, and/or a suspension that includes the one or more analytes and the one or more contaminants. For example, the sample can be a biological fluid (or biofluid), including saliva, sweat, tears, interstitial fluid, blood, or urine. The system 10 provides a way to account for the contaminant while detecting the analyte.

The system 10 can include two or more sensors (shown as sensor 1 12 and sensor 2 14). Sensor 1 12 can detect the analyte and the contaminant. Sensor 2 14 can detect the analyte or the contaminant. Sensor 1 12 can send a signal to a detection unit 16 that includes information about the analyte and the contaminant. Sensor 2 14 can send a signal to the detection unit 16 that includes information about the analyte or the contaminant. The detection unit 16 can compare the signal from Sensor 1 12 to the signal from Sensor 2 14 and determine the concentration of the analyte in the sample, which is adjusted based on the presence of the contaminant. The system 10 can provide an improved operational range, sensitivity, repeatability, and/or selectivity compared to traditional analyte biosensors, which do not adjust for the presence of the contaminant in the sample.

Sensor 1 12 can be specific for the analyte. For example, Sensor 1 12 can be indirectly sensitive for the analyte, in that Sensor 1 12 can detect a reaction product caused by interaction with a part of a recognition component of Sensor 1 12 (which can include tissue, microorganisms, organelles, cell receptors, enzymes, antibodies, nucleic acids, or the like) and the analyte. For example, the reaction product can be from an enzyme-catalyzed reaction. The enzyme can be, for example, glucose oxidase (when the analyte is glucose), lactate oxidase (when the analyte is lactate), or any other enzyme that catalyzes a reaction with the analyte. However, in some instances, the reaction product can be the same as or similar to the contaminant. In these instances, Sensor 1 12 can detect the presence of the analyte (or indirectly, the reaction product) and the contaminant in the sample. Sensor 2 14 can be specific for either the analyte or the contaminant in the sample without being sensitive for the other of the analyte or the contaminant. In some instances, Sensor 1 12 and Sensor 2 14 can be separated by a distance sufficient to prohibit diffusion of the reaction product to Sensor 2.

The system 10 can also include additional sensors that can be specific for additional elements. For example, a sensor can be sensitive to the environment (providing environmental data, like temperature, humidity, pressure, and the like) or a condition of the sample (providing sample data, like pH, ionic strength, bacterial load, microorganism load, oxygen content, protein content, reducing agents, and the like). As another example, a sensor can be specific to an agent indicating an infection. While knowing that the system 10 can include any number of sensors, only Sensor 1 12 and Sensor 2 14 are described herein.

The system 10 can include a mechanism to provide the sample to the Sensor 1 12 and Sensor 2 14. In some instances, Sensor 1 12 and Sensor 2 14 can be put into an environment with a previously collected sample. In other instances, Sensor 1 12 and Sensor 2 14 can be put into an environment to collect the sample. In either instance, the sample can be preprocessed (e.g., using a filter device) to prepare the sample for exposure to Sensor 1 12 and Sensor 2 14. For example, the filter device can remove at least 10 percent of the contaminant from the sample. As another example, the filter device can remove at least 30 percent of the contaminant from the sample. In a further example, the filter device can remove at least 50 percent of the contaminant from the sample.

The sample can cover Sensor 1 12 and Sensor 2 14, either together or sequentially. Sensor 1 12 and Sensor 2 14 can each include an electrode with one or more layers to detect the analyte and/or the contaminant in the sample. For example, Sensor 1 12 can include an electrode with layers atop the electrode to detect an analyte and a contaminant in the sample, while Sensor 2 14 can include an electrode with layers atop the electrode to detect only the analyte or only the contaminant in the sample. The electrodes described in connection with Sensor 1 12 and Sensor 2 14 can be "working electrodes", which can also be referred to as sensing electrodes. In some instances, Sensor 1 12 and/or Sensor 2 14 can be an electrochemical sensor that includes the working electrode, a counter electrode (also referred to as an auxiliary electrode), and a reference electrode to control a potential applied. In other instances, Sensor 1 12 and/or Sensor 2 14 can be an impedance sensor that includes a working electrode (or sensing electrode) and a counter electrode (also referred to as an auxiliary electrode).

Figure 2:
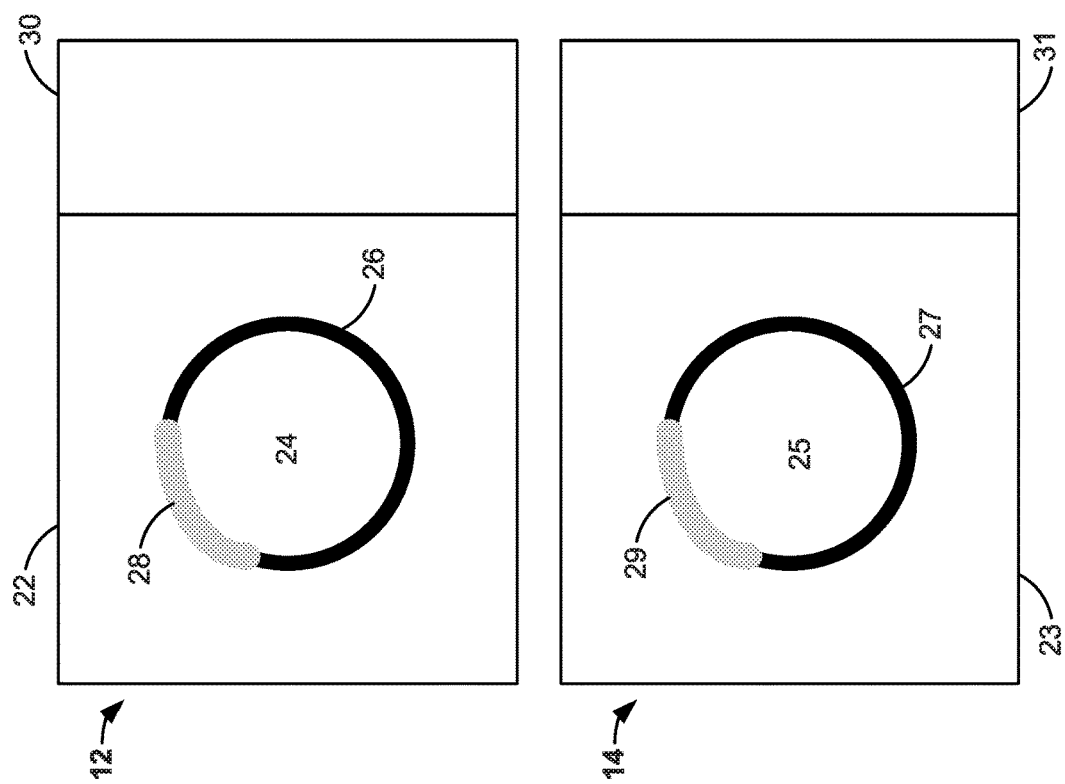
FIGS. 2 and 3 are block diagrams showing example implementations of the sensors shown in FIG. 1.
Figure 3:
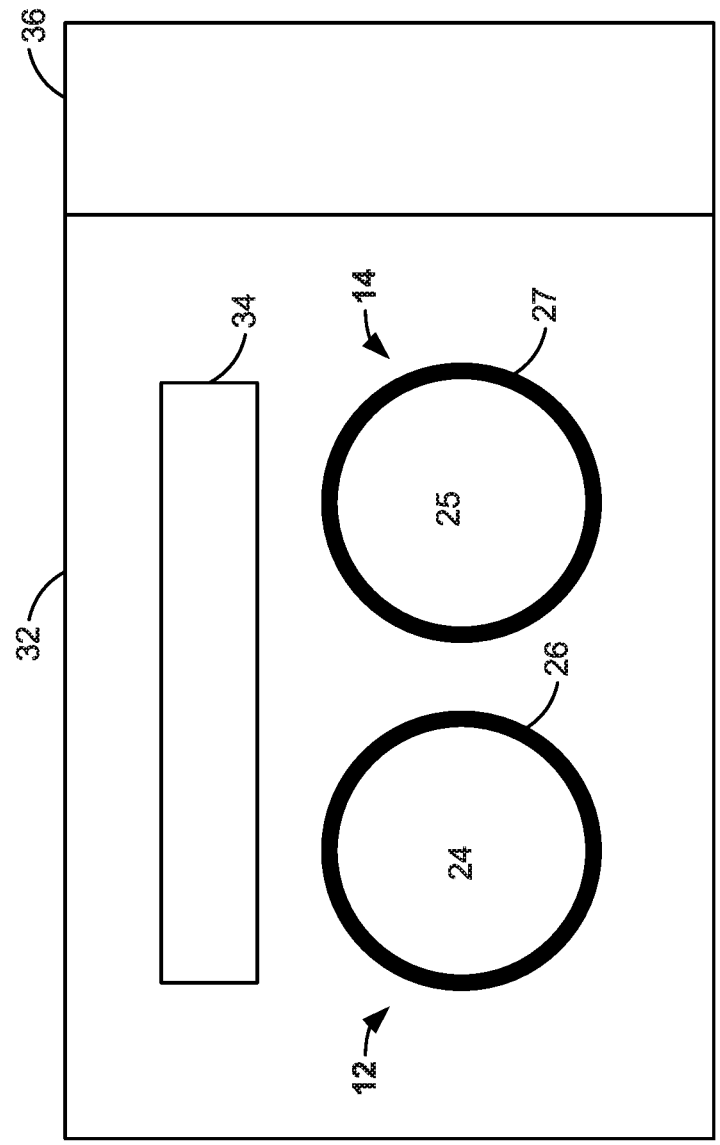

In some instances, Sensor 1 12 and Sensor 2 14 can be arranged in an array. Additional sensors can be arranged in the array or separate from the array. Sensor 1 12 and Sensor 2 14 can be embodied in a single chip configuration, shown in FIG. 2 (however, the specific design being on the chip is not necessary), or a double chip configuration, shown in FIG. 3 (however, the specific design being on the chip is not necessary). In the examples of FIGS. 2 and 3, the Sensor 1 12 and Sensor 2 14 are illustrated as electrochemical sensors. Sensor 1 12 and Sensor 2 14 can be arranged in different configurations than those shown in FIGS. 2 and 3. In one example, Sensor 1 12 and Sensor 2 14 can be concentric to one another instead of being arranged side-by-size. The concentric arrangement can reduce the volume of the sample needed.

In the examples shown in FIGS. 2 and 3, Sensor 1 12 and Sensor 2 14 must be separated by a distance far enough such that a reaction product does not diffuse to the other sensor. For example, the distance separating the Sensor 1 12 and Sensor 2 14 can be a square root of a diffusion coefficient of the reaction product. As another example, the distance separating Sensor 1 12 and Sensor 2 14 can be at least 150 µm. In a further example, the distance separating Sensor 1 12 and Sensor 2 14 can be at least 200 µm. In some instances, the distance can be provided by a physical barrier between Sensor 1 12 and Sensor 2 14.

In FIG. 2, each chip (including one of Sensor 1 12 and Sensor 2 14) includes a substrate 22, 23 (which can be non-conductive or semi-conductive) and an electrical connector 30, 31. The sensors 12 and 14 can be positioned on each substrate 22, 23 so that at least a portion of the sample can cover the electrodes of Sensor 1 12 and Sensor 2 14. The electrodes can include working electrodes 24, 25, counter electrodes 26, 27, and reference electrodes 28, 29.

In FIG. 3, a single chip can include both Sensor 1 12 and Sensor 2 14. The single chip can include a substrate 32 (which can be non-conductive or semi-conductive) and an electrical connector 36. The sensors 12 and 14 can be positioned on the substrate 32 so that at least a portion of the sample can cover the electrodes of each of Sensor 1 12 and Sensor 2 14. The electrodes can include working electrodes 24, 25, counter electrodes 26, 27, and a shared reference electrode 34.

In either of the illustrations in FIG. 2 or FIG. 3, the working electrodes 24, 25 can be covered by one or more layers to facilitate the detection of the analyte and/or the contaminant. The working electrode 24 can include a layer sensitive to the analyte and another layer sensitive to the contaminant. For example, in the case of a biosensor detecting the analyte indirectly, the layers can include a layer that starts a reaction of the analyte and a layer that detects the reaction product. In cases where the reaction product is the contaminant, the layer that detects the reaction product can detect the contaminant within the sample as well. The working electrode 25 can include a layer sensitive to the analyte (or the analyte and the contaminant) or another layer sensitive to the contaminant.

An example of layers that can be positioned atop the working electrodes 24 and 25 is shown in FIG. 4. Each of the working electrodes 24, 25 can include a base layer 42 that is placed atop the working electrode 24, 25 that is selective to the contaminant. The working electrode 24 can include a middle layer 44 atop the base layer and a top layer 46 atop the middle layer 44 with a component that can bind to the middle layer 44. The top layer 46 can be selective to the analyte and the contaminant. For example, the top layer 46 or the middle layer 44 can include an enzyme that facilitates a reaction with the analyte to produce a reaction product that is detected by the base layer 42. The working electrode 25 may include the middle layer 44, but need not include the middle layer 44.

Referring again to FIG. 1, the system 10 can also include a detection unit 16 device that includes a processor 18. For example, the processor 18 can be a microprocessor. In some instances, the detection unit 16 device can also include a non-transitory memory that can store instructions that are executable by the processor 18. For example, the non-transitory memory can be a random access memory device. However, the non-transitory memory need only be a memory that is not a transitory signal.

The detection unit 16 device can receive signals from Sensor 1 12 and Sensor 2 14, with one signal indicating the detection of the analyte and the contaminant and the other signal indicating the detection of the analyte or the contaminant. The signals from the Sensor 1 12 and Sensor 2 14 can be transmitted wirelessly and/or according to a wired connection between Sensor 1 12 and Sensor 2 14 and the detection unit 16 device. For example, the signals can be sent according to a timing between Sensor 1 12 and Sensor 2 14. The timing can be that the signals are measured at different times, controlled by an electronic or physical mechanism (e.g., space between Sensor 1 12 and Sensor 2 14, which may be defined by diffusion of the analyte or contaminant, a controlled flow from Sensor 1 12 to Sensor 2 14, or the like).

The detection unit 16 device can determine a concentration of the analyte or the contaminant by comparing the signals according to an algorithm. In some instances, the signals can experience signal conditioning 19 before the signals are transmitted to the detection unit 16 device. The signal conditioning 19 can occur within the detection unit 16, as illustrated, but can also occur before the signals reach the detection unit 16. As one example, the signal conditioning 19 can be a noise removal process. In another example, the signal conditioning 19 can be a normalization of the data between the two signals.

Figure 5:
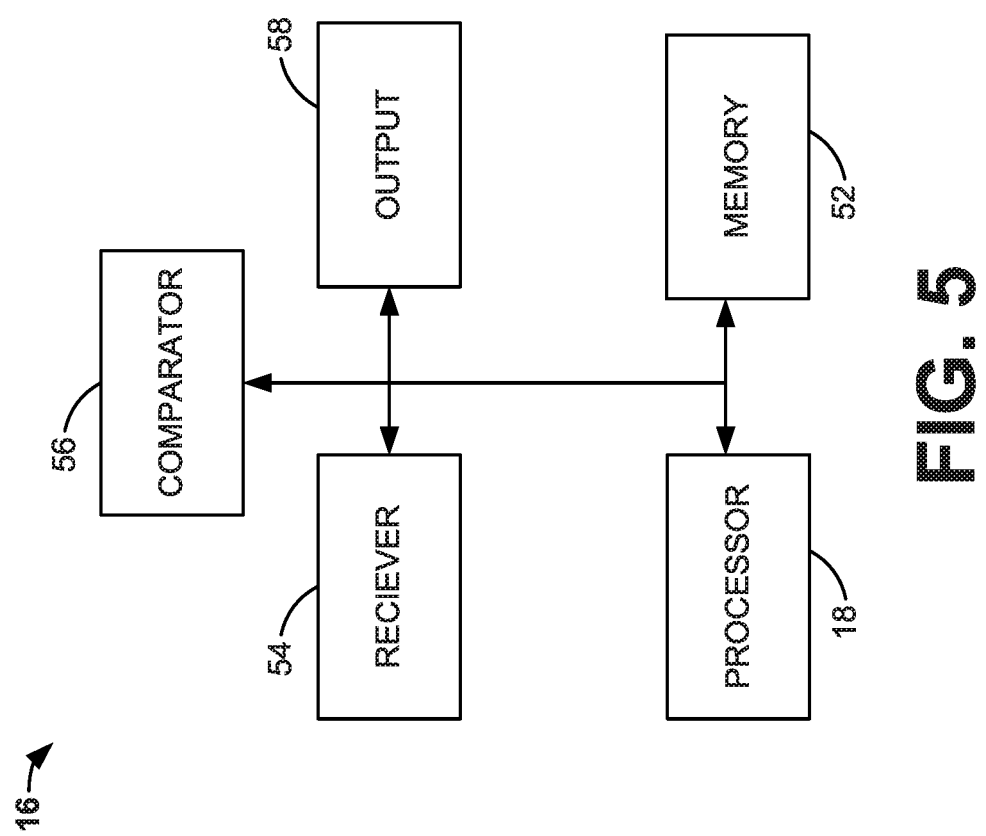
FIG. 5 is a block diagram showing an implementation of the processing of the detection unit shown in FIG. 1.

Processing conducted by the detection unit 16 is shown in greater detail in FIG. 5. The processor 18 can access the memory 52 to execute instructions related to an algorithm for determining the concentration of the analyte or the concentration of the contaminant. The steps are implemented as a receiver 54, a comparator 56, and an output 58. The receiver 54 can receive signals from sensors 12 and 14 indicating detection of the analyte and/or the contaminant. The comparator 56 can either filter a concentration of a contaminant out of the concentration of the analyte or filter a concentration of the analyte out of the concentration of the contaminant. For example, the comparator 56 can take an absolute value of a difference between the signals from the sensors 12, 14. The output 58 can output the associated concentration of the analyte or contaminant and/or any additional information in a form that can be perceived through a user's senses. For example, the output can be an audio output, a video output, or the like. In some instances, the detection unit 16 device can be configured with a display unit for a visual display and/or speakers for an audio display.

In some instances, when the system 10 includes a sensor that detects data related to the environment, the processor 18 can correct the determined concentration of the analyte or contaminant based on the data related to the environment. In other instances, when the sample is a biological sample and the analyte is glucose, the detection unit 16 device can determine if the patient associated with the biological sample is diabetic, normal, or has an infection causing a spike in glucose concentration based on a signal from a sensor that detects an infective agent. In still other instances, the detection unit 16 device can determine whether an organ is in failure based on the analyte concentration.

Figure 6:
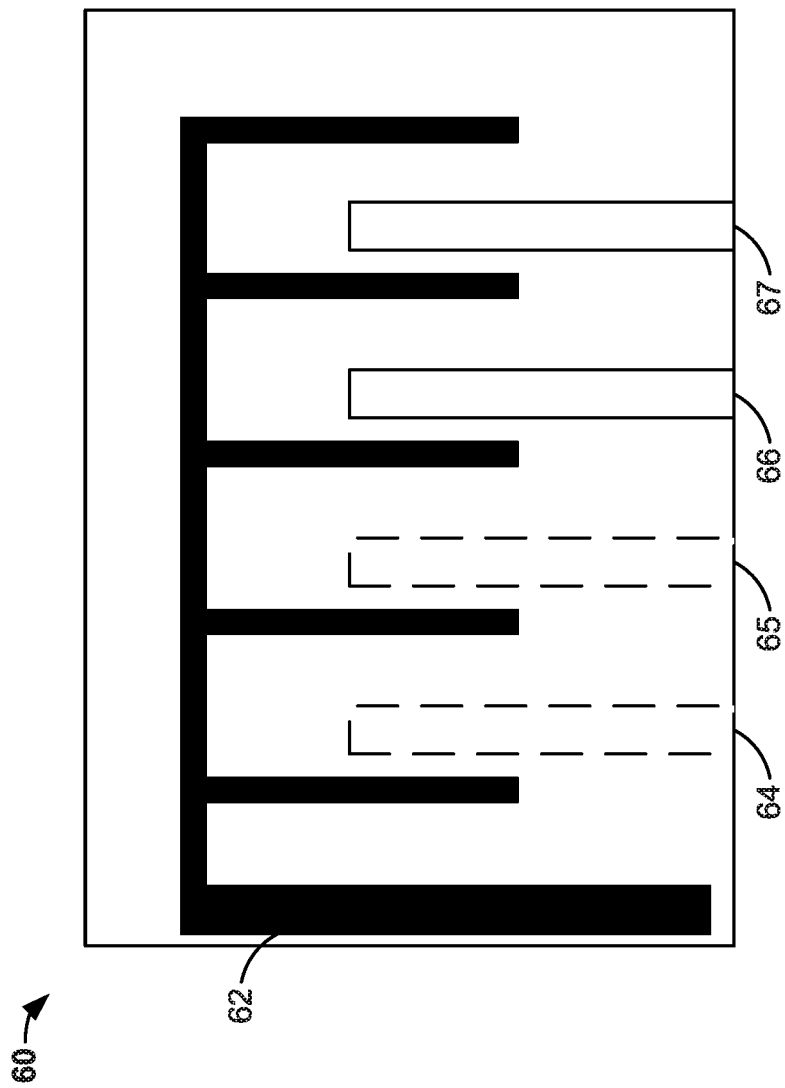
FIG. 6 is a block diagram showing an example implementation of the sensors shown in FIG. 1 arranged as an array with the sample flowing over the array.

FIG. 6 shows one example 60 implementation of the system 10. Other example implementations are possible. As an example, the system 60 can be a test strip. The example 60 includes a channel 62 that facilitates the flow of the sample over elements 66, 67 (which can include Sensor 1 12 and Sensor 2 14). Elements 64 and 66 can be optional filter elements that can reduce the concentration of the contaminant. The channel 62 can facilitate the flow, for example, through capillary forces, mechanical forces, piezoelectric forces, mechanical pumping forces, application of differential pressure, or the like. The sample can be flowed over one or more of the elements 64 and 65 to remove at least a portion of the contaminant before the sample reaches elements 66 and 67 (sensors 12 and 14) for detection of the analyte and/or contaminant.

IV. Methods

Another aspect of the present disclosure can include methods 70 and 80 (FIGS. 7 and 8) for detecting the presence of an analyte in a contaminated sample. As an example, the methods 70 and 80 can be executed using the system 10 shown in FIG. 1 and described above. Advantageously, the methods 70 and 80 can be used detect an analyte and filter out a contaminant.

The methods 70 and 80 are illustrated as process flow diagrams with flowchart illustrations. For purposes of simplicity, the methods 70 and 80 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 70 and 80.

Figure 7:
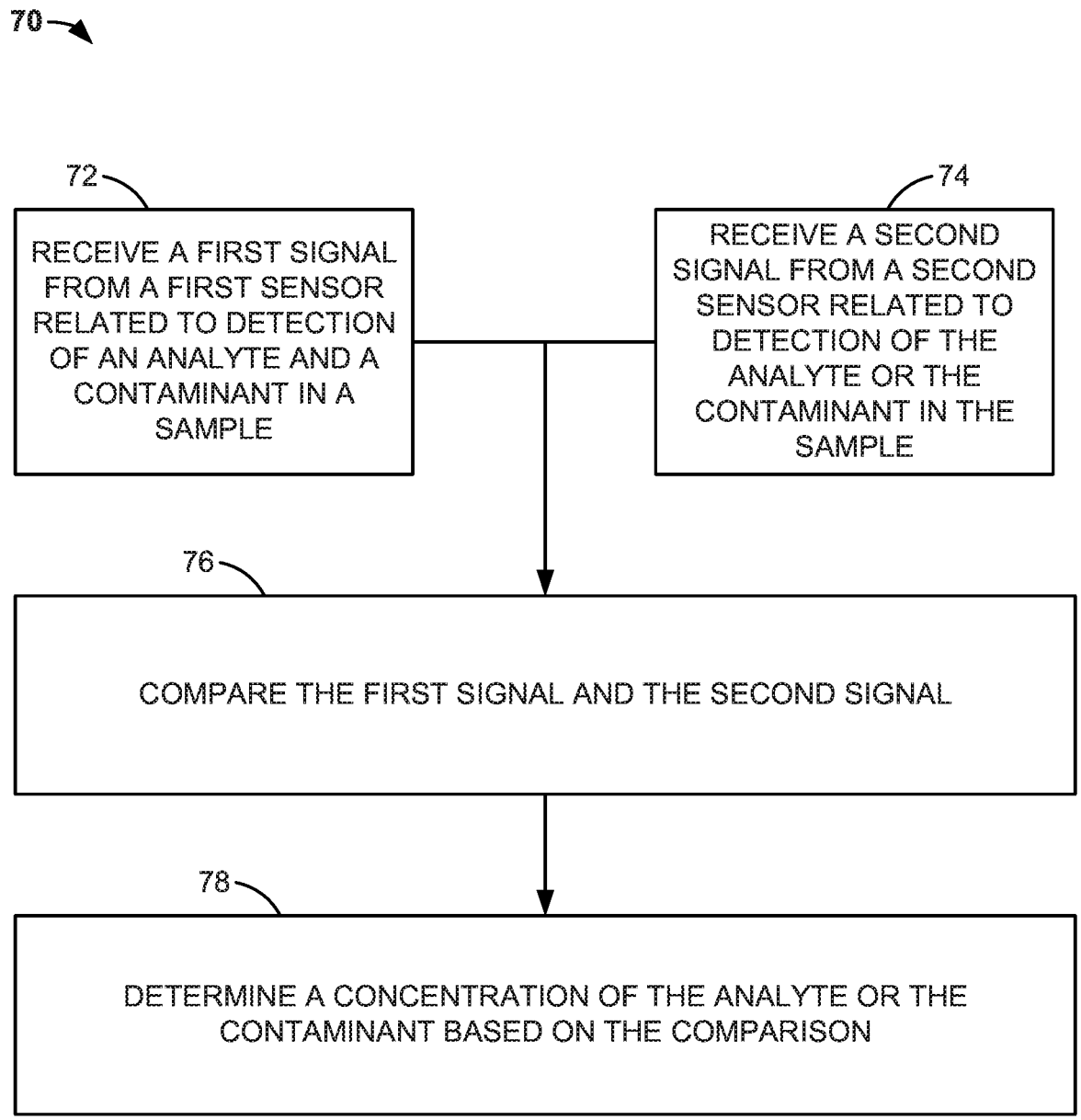
FIG. 7 is a process flow diagram showing an example method for detecting the presence of an analyte or a contaminant in a contaminated sample according to another aspect of the present disclosure.

Referring now to FIG. 7, illustrated is a method 70 for detecting the presence of an analyte in a contaminated sample. At Step 72, a first signal can be received (by a detection unit 16) from a first sensor (e.g., Sensor 1 12) related to detection of an analyte and a contaminant in a sample. The first sensor can include a first electrode and one or more first layers atop the first electrode configured to detect the analyte and the contaminant in the sample. It will be understood that the first sensor also includes a counter electrode and a reference electrode. At Step 74, a second signal can be received (by the detection unit 16) from a second sensor (e.g., sensor 2 14) related to detection of the analyte or the contaminant in the sample. The second sensor can include a second electrode and one or more second layers atop the second electrode to detect the analyte or the contaminant in the sample. It will be understood that the second sensor also includes a counter electrode and a reference electrode. In some instances, the reference electrode can be shared between the first and second sensor.

The signals can undergo signal processing or signal conditioning (e.g., by the signal conditioning unit 19 within the detection unit 16). At Step 76, the first signal and the second signal can be compared (e.g., by the processor 18 of the detection unit 16). In some instances, the signals can only be compared after a normalization is performed in each of the signals.

At Step 78, a concentration of the analyte or the contaminant can be determined (e.g., by the processor 18 of the detection unit 16) based on the comparison. For example, the comparison can remove the analyte or the contaminant from the first signal based on the second signal. The concentration of the analyte or the contaminant can be determined based on an algorithm configured for detection of the analyte or the contaminant. For example, when determining glucose concentration in the presence of a hydrogen peroxide contaminant, the algorithm can include subtracting the hydrogen peroxide concentration from the saliva from the hydrogen peroxide concentration of a sensor the detects hydrogen peroxide formed from a glucose oxidase reaction and the hydrogen peroxide in the mouth. This concentration can be output as an audio signal and/or a visual signal.

Figure 8:
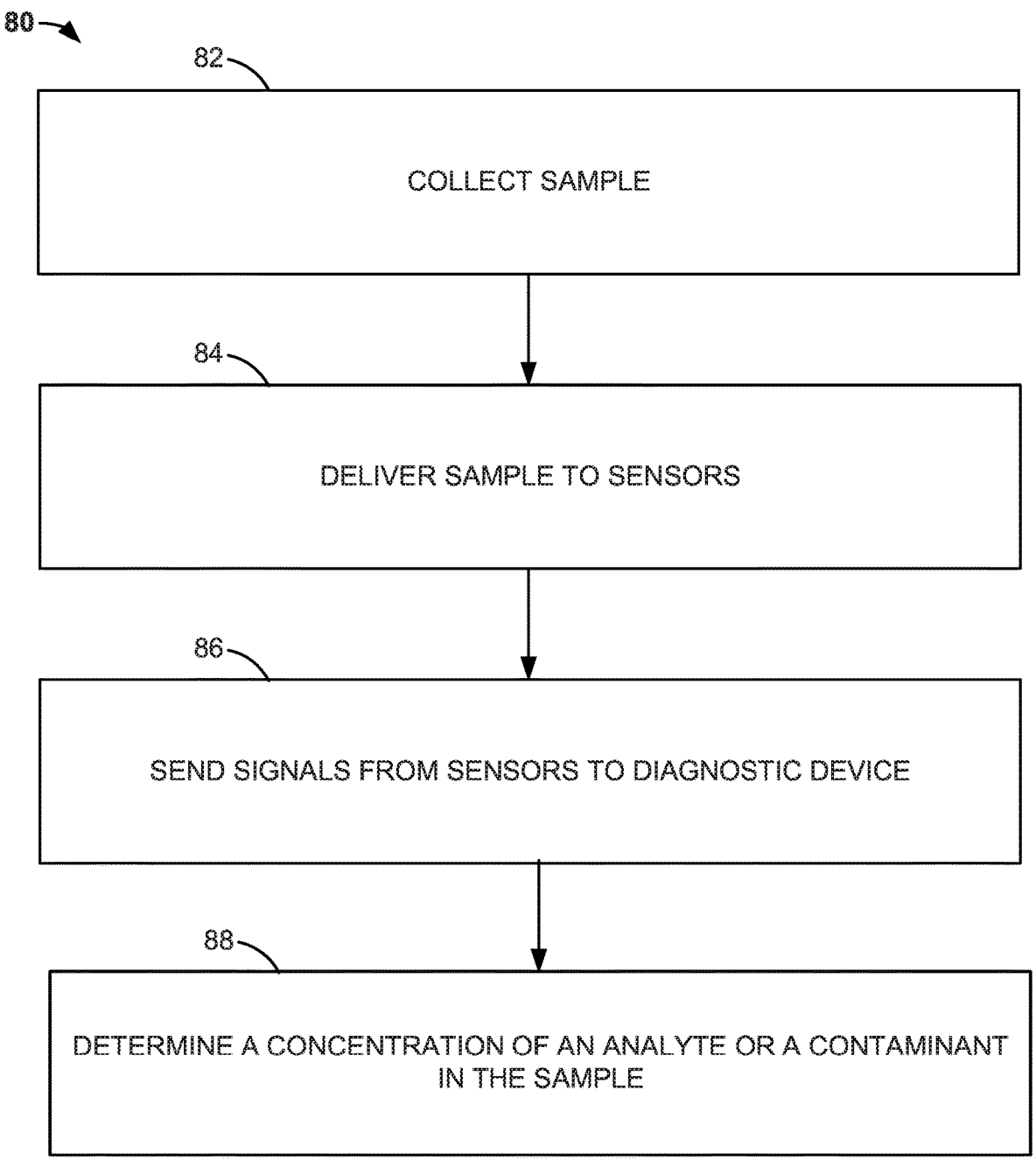
FIG. 8 is a process flow diagram showing an example method for performing the method of FIG. 7.

Referring now to FIG. 8, illustrated is another method for detecting the presence of an analyte in a contaminated sample. At Step 82, a sample can be collected. At Step 84, the sample can be delivered to two or more sensors. The two or more sensors, in some instances, can be arranged in an array. In some instances, the sample can be filtered before it is delivered to the two or more sensors. At Step 86, signals can be transmitted from the sensors to the diagnostic device. One of the sensors can detect the presence of the analyte and the contaminant. The other of the sensors can detect the presence of the analyte or the contaminant. At Step 88, a concentration of the analyte or the contaminant in the sample can be determined. The determination can be made at a diagnostic device according to an algorithm, where the first signal and the second signal are compared and processed. The concentration can be output as an audio, visual, or digital including graphical signal.

V. Proposed Configurations

Figure 9:
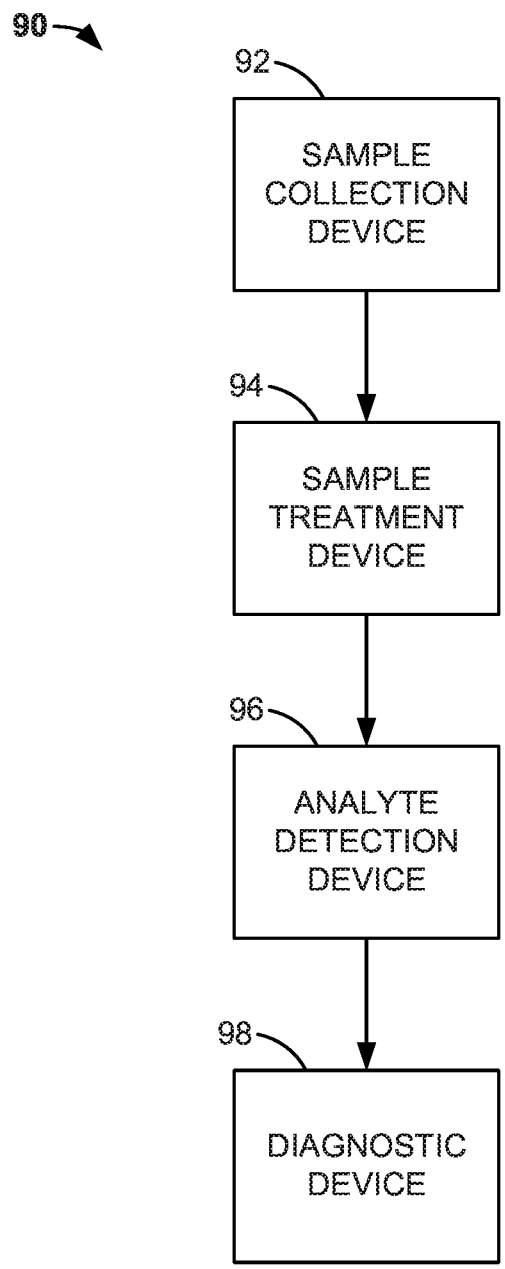
FIG. 9 is a block diagram showing an example group of devices that can be used to detect a biomarker in a contaminated sample.

FIG. 9 shows an example group 90 of devices that can be used to detect a biomarker in a contaminated sample. The group 90 of devices can include, but is not limited to, a sample collection device 92, a sample treatment device 94, an analyte detection device 96 (which can also detect a contaminant), and a diagnostic device 98. The sample collection device 92 can collect a volume of the sample for analysis. The sample treatment device 94 can provide a filter to remove a portion of the contaminant from the sample. The analyte detection device 96 can include the sensors (e.g., Sensor 1 12, Sensor 2 14, and any additional sensors) to detect the analyte and the contaminant in the sample (as described above). The sensors can provide a signal reflecting the detection of the analyte and the contaminant and a signal reflecting the detection of the analyte or the contaminant. The diagnostic device 98 can process the signals and determine the presence of the analyte or the contaminant based on the signals. The diagnostic device 98 can also output the determined concentration of the analyte or the contaminant in the sample in a human comprehensible form (e.g., audio, visual, or the like).

Figure 10:
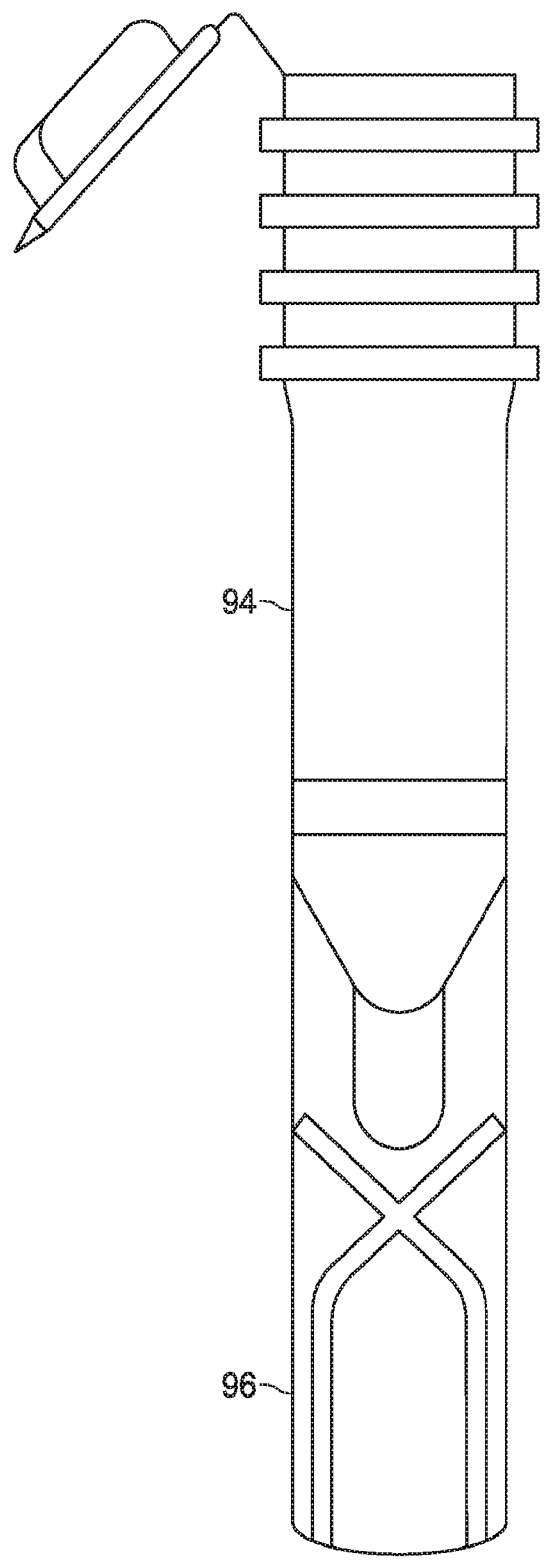
FIG. 10 is a sketch of an example collection device and sensor system.
Figure 11:
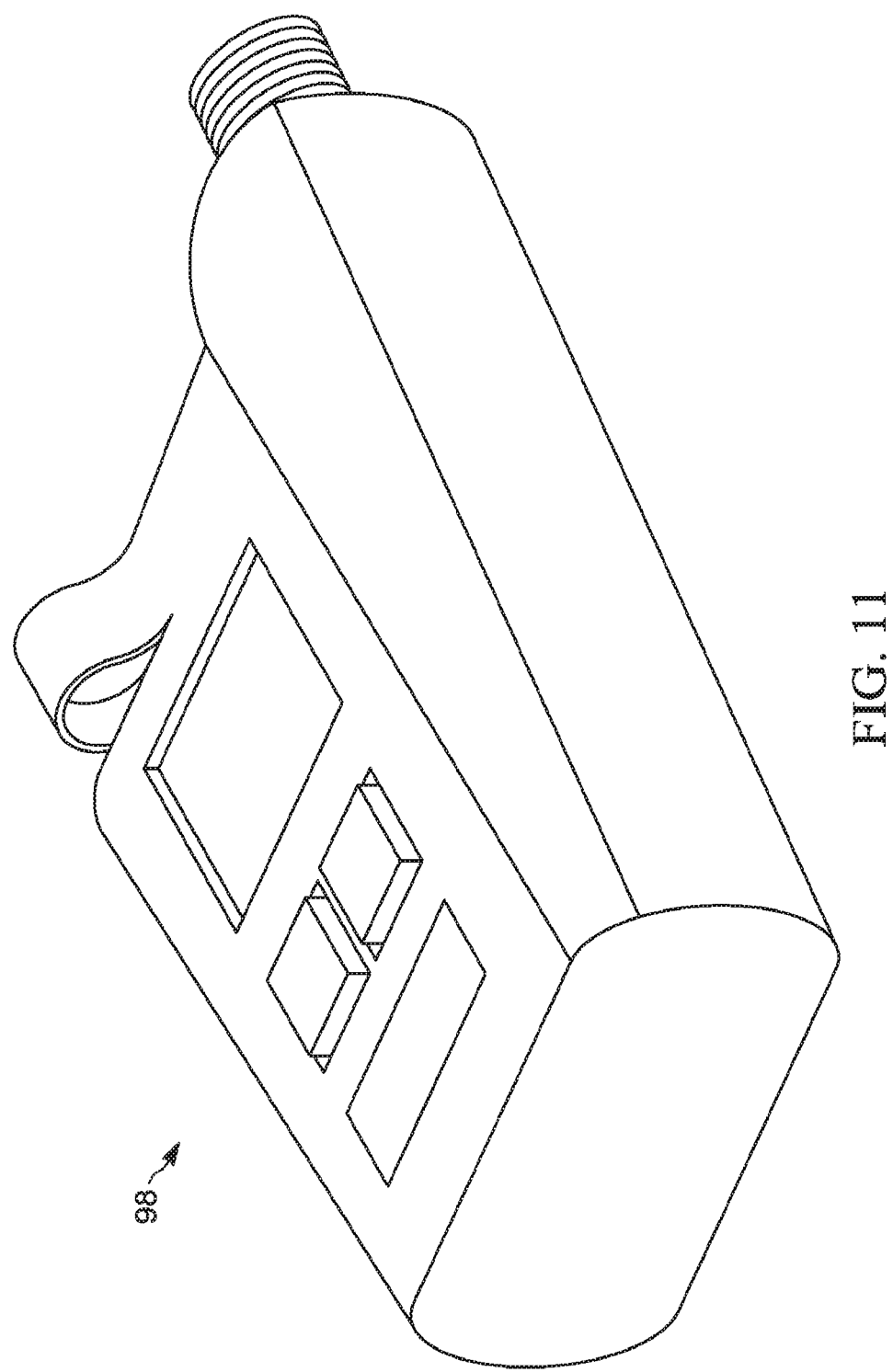
FIGS. 11-13 are sketches of example diagnostic devices.
Figure 12:
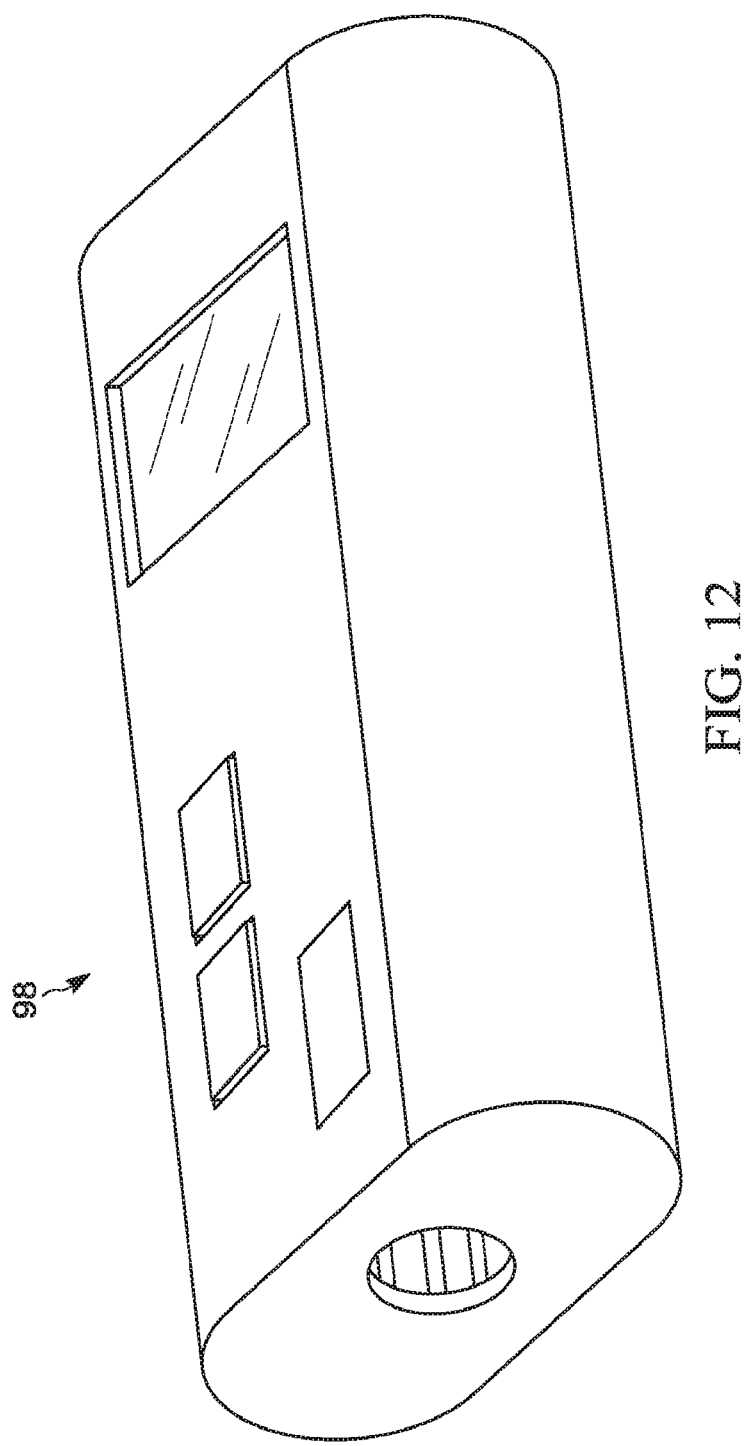
Figure 13:
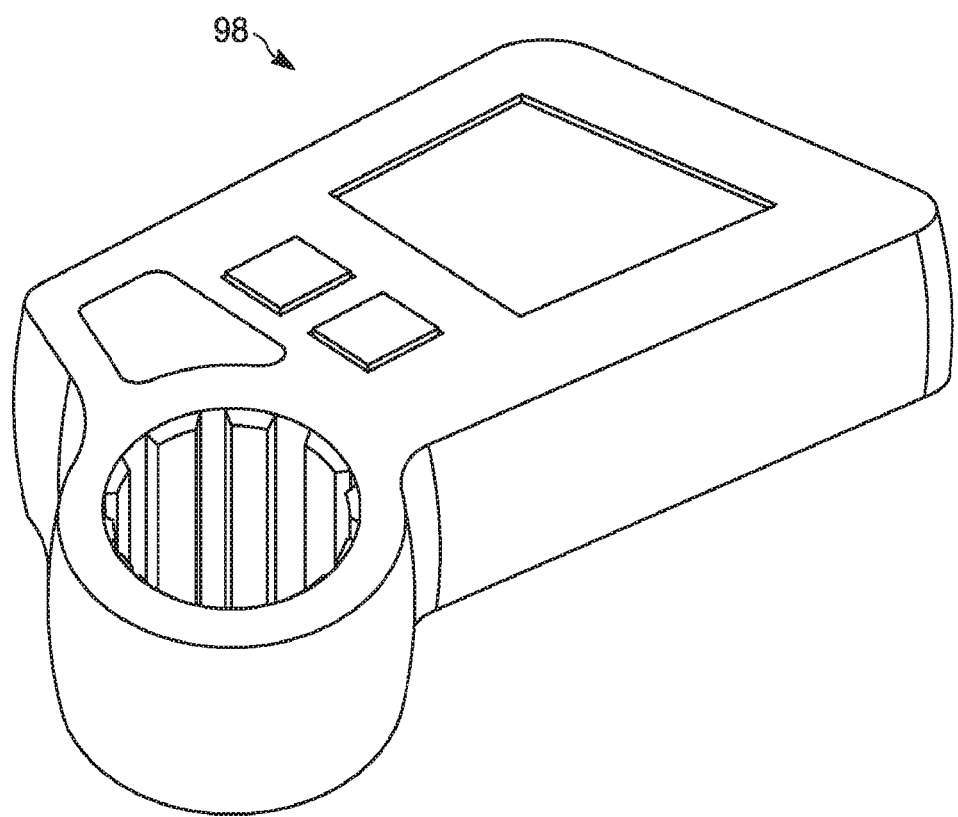

In some instances, devices of the group 90 of devices can be implemented as distinct, separate devices. In other instances, a portion of the devices can be embodied together (as the test strip in FIG. 6, as devices in FIGS. 10-13, or in any other embodiment not described herein). The test strip of FIG. 6 includes the sample collection device 92 (which can collect the liquid sample directly without processing), the sample treatment device 94 (this is an optional component), and the analyte detection device 96. The diagnostic device 98 can be implemented as a separate device. The group 90 of devices can be implemented in a different form in FIGS. 10-13. A distinct sample collection device 92, a device shown in FIG. 10 that includes the sample treatment device 94 and the analyte detection device 96, and a device shown in FIG. 11 or 12 that includes the diagnostic device 98. For example, the sample can be collected by an absorbent swab. The swab can be placed in the device of FIG. 10, and the sample drained from the swab. As another example, the sample can be obtained directly as a liquid sample (e.g., via passive drool). In some instances, the sample can proceed through the sample treatment device 94 (however, the sample treatment device 94 is unnecessary). The sample can then cover the sensors of the analyte detection device 96. The analyte detection device 96 includes at least two sensors, one to detect the analyte and contaminant and one to detect the analyte or contaminant (and can include other sensors to detect other factors related to the sample, the environment, etc.). The analyte detection device 96 can be inserted into the detection device of FIGS. 11-13, and the signals from the sensors can be processed and the concentration of the analyte or the contaminant can be output in a human comprehensible form.

VI. Examples

The following example illustrates glucose detection by a salivary biomarker diagnostic device, which can be used as for point-of-care monitoring and diagnostic applications. Glucose detection is a valuable tool in the management of diabetes mellitus, a leading cause of morbidity and mortality worldwide. Without proper treatment, diabetes can result in serious complications including kidney failure, stroke, heart attach, high blood pressure, blindness, and coma. However, the frequency and severity of these complications can be reduced through continuous diabetes management. Regular and frequent daily measurements of blood glucose levels in diabetic patients are critical in optimizing treatment and reducing complications. Consequently, point-of-care glucose biosensors are commonly used to monitor glucose levels in both inpatient and outpatient settings and play an integral role in diabetes management.

Standard point-of-care glucose biosensors require a small blood sample obtained by a finger prick, which is painful and disrupts the patient's daily life. The finger prick has a low compliance and a low long-term sustainability. Consequentially, significant effort has been made to develop non-invasive glucose biosensors. One proposed potential non-invasive glucose biosensor is a salivary glucose biosensor. Salivary glucose levels have been shown to be elevated in diabetic process, and these salivary glucose levels have been shown to correlate reasonably well with blood glucose levels. Thus, the use of saliva in glucose detection could provide a viable alternative to standard blood glucose sensors. However, limitations currently exist with the use of saliva in glucose biosensors. Notably, human saliva contains contaminants, such as hydrogen peroxide, which may interfere with glucose detection. The presence of hydrogen peroxide in saliva can lead to erroneously high glucose measurements, resulting in sub-optimal treatment and increased patient morbidity and mortality. The salivary biomarker diagnostic device described in the following example can accurately detect and measure glucose in saliva in the presence of a contaminant. It should be noted that, although these experiments were directed to glucose, other biomarkers can be detected in a similar manner.

Glucose Sensor Architecture

The glucose sensor used in this experiment measures the concentration of hydrogen peroxide ($H_2O_2$) to make an indirect determination of the concentration of glucose in saliva. The glucose sensor includes three electrodes—a reference electrode, a working electrode, and a counter electrode. In this example, the reference electrode is a silver (Ag) electrode or a platinum (Pt) electrode. The counter electrode is a carbon (C) electrode or a platinum (Pt) electrode. The working electrode has layers thereupon, as shown in FIG. 4, with a base layer 42 that includes carbon nanotubes to detect hydrogen peroxide, a middle layer 44 that includes chitosan, and a top layer 46 that includes glucose oxidase (GOx) and gold nanoparticles that bind to the chitosan of the middle layer 44.

Glucose Oxidase (GOx)

GOx catalyzes a chemical reaction between glucose and oxygen to form D-glucono 1,5-lactone and $H_2O_2$.

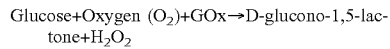

Glucose+Oxygen ($O_2$)+GOx→D-glucono-1,5-lactone+$H_2O_2$

The glucose sensor can detect the $H_2O_2$ generated by this chemical reaction.

The reaction between GOx and glucose can be controlled electrochemically by methods including, but not limited to, cyclic voltammetry (CV) or chronoamperometry. CV is an electrochemical technique in which the working electrode potential is ramped linearly versus time and, after a set potential is reached, the working electrode potential is ramped in the opposite direction to return to the initial potential. Chronoamperometry is an electrochemical technique in which the potential of the working electrode is stepped and the resulting current from faradaic processes occurring at the electrode (caused by the potential step) is monitored as a function of time.

Glucose Sensor in PBS

Figure 14:
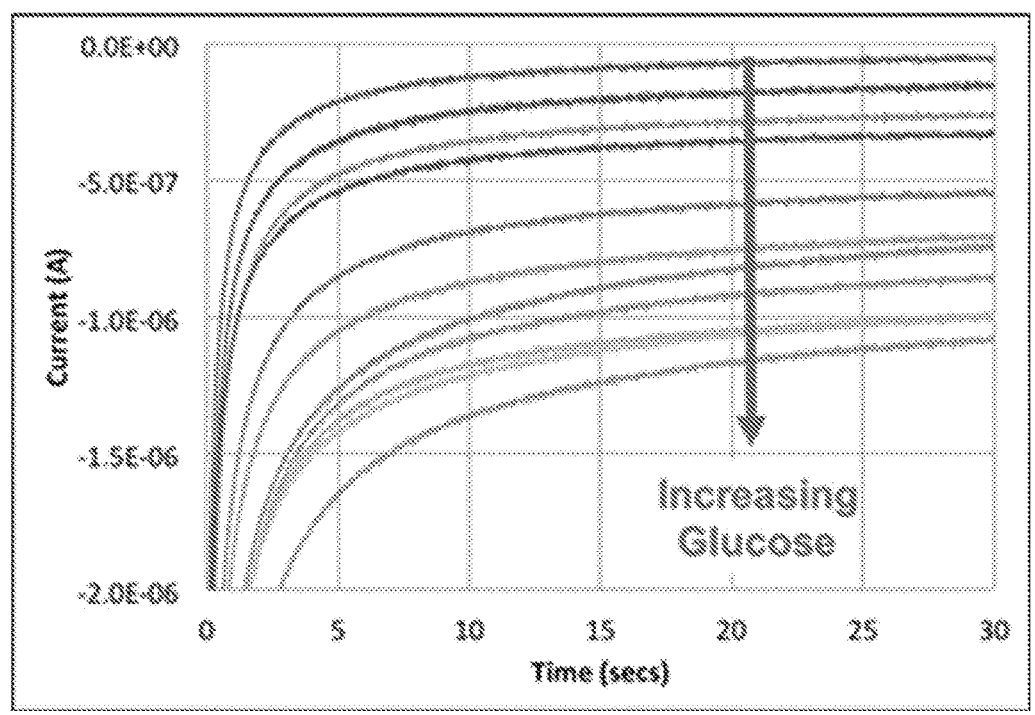
FIG. 14 is a plot showing chronoamperometry of a glucose sensor with increasing concentrations of glucose in PBS.

The glucose sensor was in the presence of 50 µL of Phosphate Buffer Solution (PBS, pH=7.0) having varying concentrations of glucose (0-10 mg/dL). Chronoamperometry (+4.0 V vs. Ag) was applied for 30 seconds at the sensor for each concentration of glucose. FIG. 14 shows the voltammogram of the raw amperometric current. As shown in FIG. 14, the current decreases with as the concentration of glucose increases. This suggests that the electrochemical measurement is of hydrogen peroxide being generated by the GOx reaction with glucose.

Figure 15:
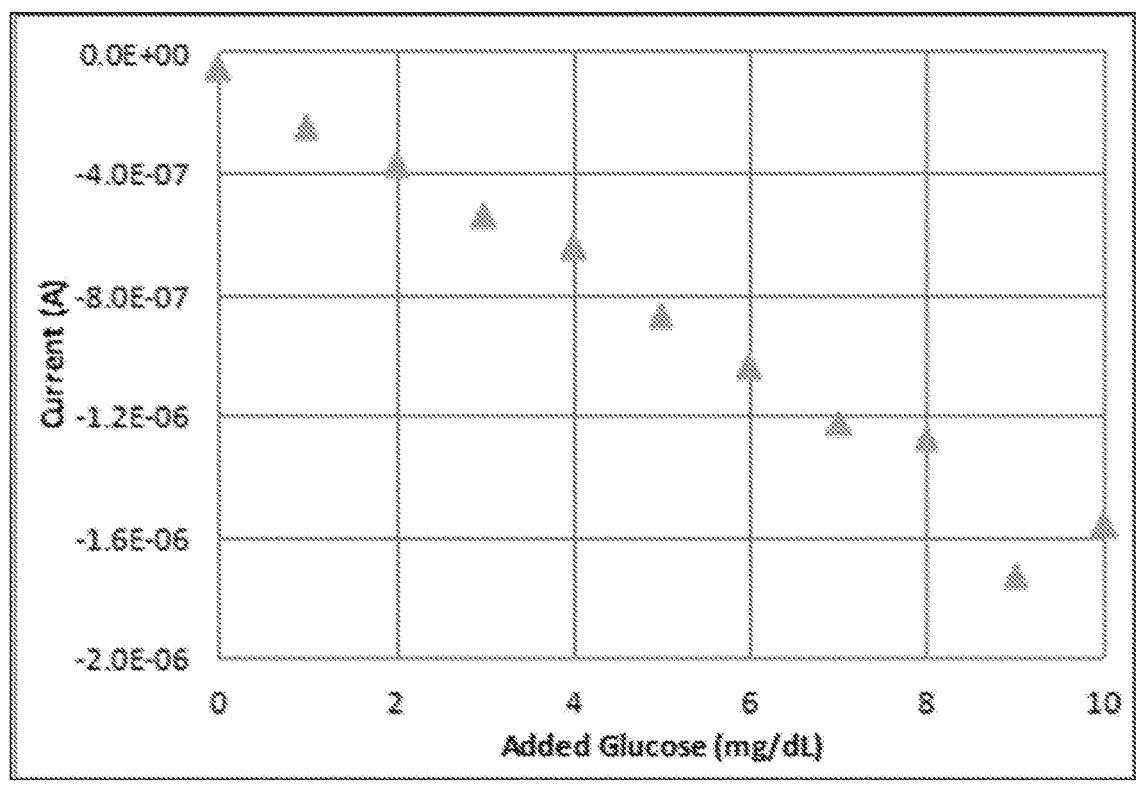
FIG. 15 is a plot showing amperometric current response at the glucose sensor in PBS containing varying concentrations of added glucose.
Figure 16:
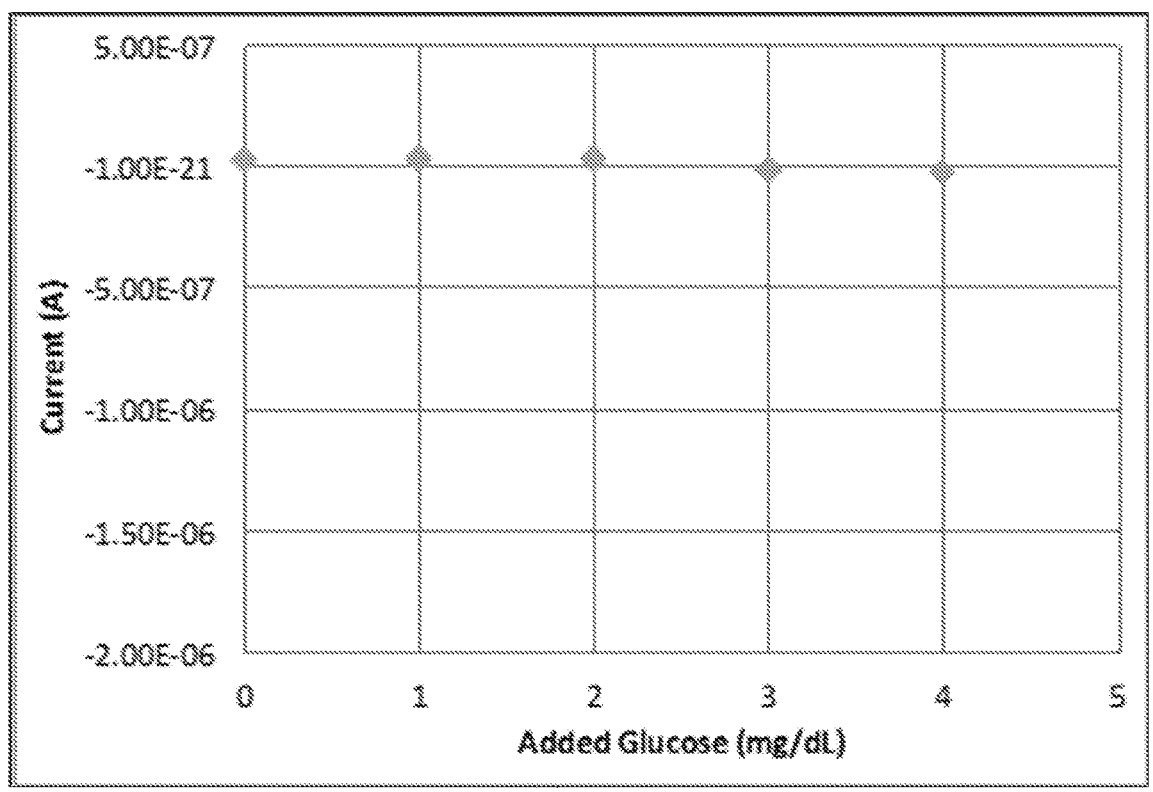
FIG. 16 is a plot showing amperometric current response at a non-glucose sensor in PBS containing varying concentrations of glucose.

When the current is plotted against concentration of added glucose (FIG. 15), the linear relationship gives a sensitivity of $1.1 \times 10^{-7}$ $Amg^{-1}dL^{-1}$. To ensure that the glucose sensor was measuring the activity of GOx, several sensors without GOx (the top layer 46) underwent the same chronoamperometry test, as described above, in the presence of 50 µL of Phosphate Buffer Solution (PBS, pH=7.0) having varying concentrations of glucose (0-4 mg/dL, pH 7.0). FIG. 16 shows the amperometric current's relationship to the added glucose. There was no observable change in the current, suggesting that the sensor is indeed detecting the hydrogen peroxide product generated by the reaction catalyzed by the GOx.

Figure 17:
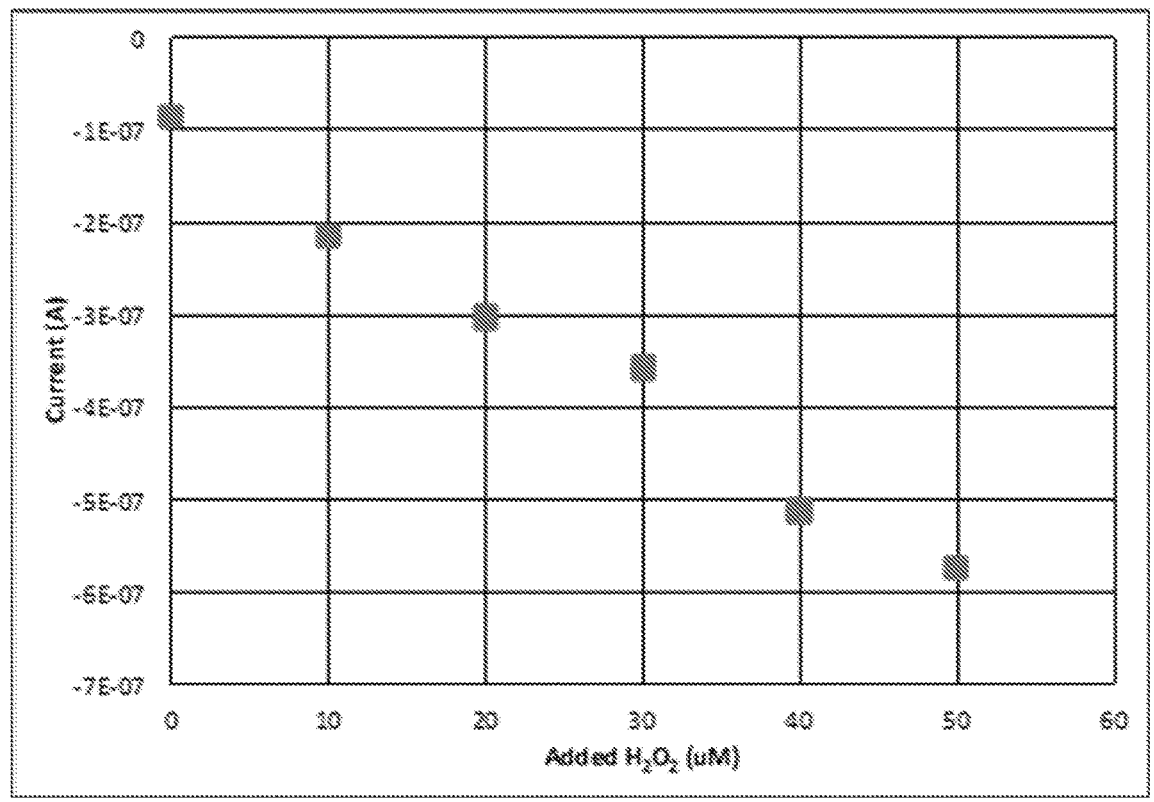
FIG. 17 is a plot showing a calibration curve of $H_2O_2$ at the glucose sensor.

Since the glucose sensor requires the indirect determination of glucose through the electrochemical measurement of hydrogen peroxide, the amperometric behavior of hydrogen peroxide at the glucose sensor was studied in the presence of 50 µL of Phosphate Buffer Solution (PBS, pH=7.0) having varying concentrations of hydrogen peroxide (0-50 mg/dL). Chronoamperometry (+4.0 V vs. Ag) was applied for 30 seconds for each concentration of hydrogen peroxide. FIG. 17 shows the amperometric current linear relationship with hydrogen peroxide, which has a sensitivity of $-9.7 \times 10^{-9}$ A $\mu M^{-1}$.

After obtaining the calibration curves of glucose (FIG. 15) and hydrogen peroxide (FIG. 17), the concentration of glucose can be determined from the amount of hydrogen peroxide produced and detected at the glucose sensor. As a proof-of-concept, buffer solutions were spiked with different amounts of glucose (amounts typically seen in human saliva) and tested using the glucose sensor. The results of this test are shown in Table 1.

TABLE 1

Recovered glucose concentrations from known spiked buffer solutions.

| Spiked Glucose in PBS (pH 7) (mg/dL) | Raw Current (A) | Recovered Glucose via $H_2O_2$ (mg/dL) |
|---|---|---|
| 1 | $-2.6 \times 10^{-7}$ | 1.6 |
| 3 | $-5.5 \times 10^{-7}$ | 2.9 |
| 5 | $-7.8 \times 10^{-7}$ | 4.4 |

The recovered glucose concentration is relatively close to that of the original spike glucose content in the PBS solution, indicating successful determination of glucose.

Non-Glucose Sensor Architecture

Real human saliva contains a concentration of hydrogen peroxide. Since the glucose sensor detects hydrogen peroxide formed in the chemical reaction to detect the concentration of glucose, a secondary sensor (referred to as a non-glucose sensor) is necessary to detect the preexisting hydrogen peroxide in the saliva.

The secondary sensor includes three electrodes—a reference electrode, a working electrode, and a counter electrode. In this example, the reference electrode is a silver (Ag) electrode or a platinum (Pt) electrode. The counter electrode is a carbon (C) electrode or a platinum (Pt) electrode. The working electrode has layers thereupon, as shown in FIG. 4, with a base layer 42 that includes carbon nanotubes to detect hydrogen peroxide, a middle layer 44 that includes chitosan, but does not include the top layer 46 that includes glucose oxidase (GOx) and gold nanoparticles that bind to the chitosan of the middle layer 44. The presence of the middle layer 44 is optional in this experiment.

Non-Glucose Sensor in PBS

Figure 18:
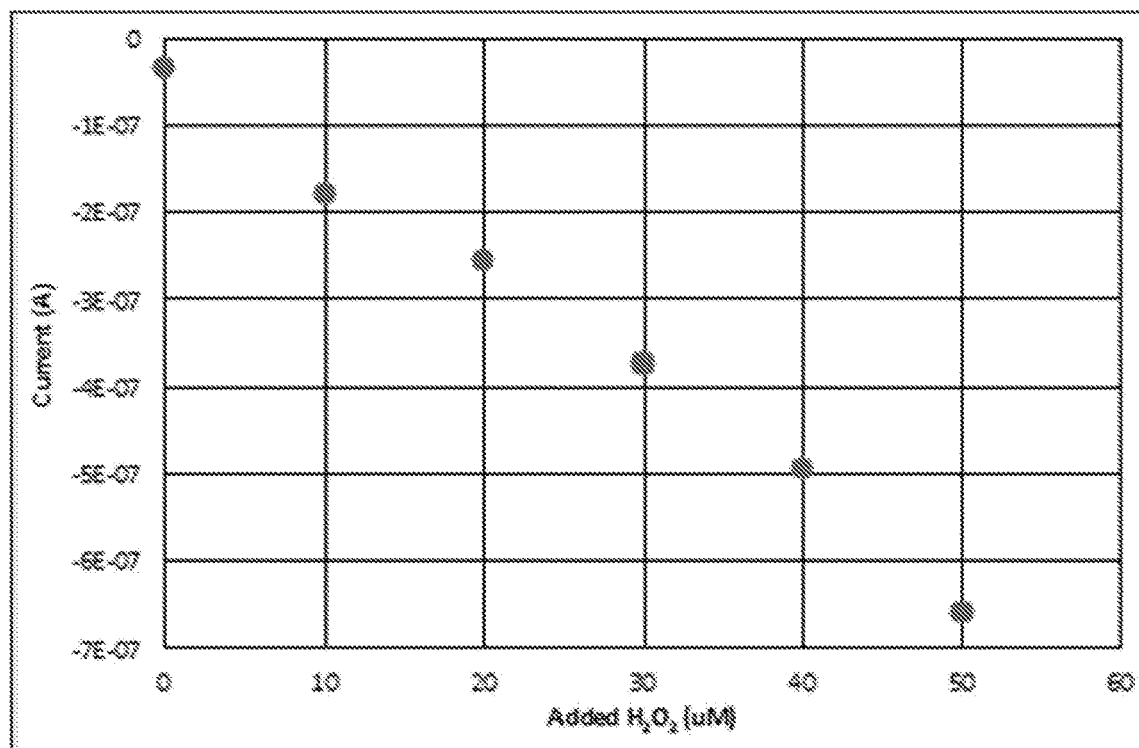
FIG. 18 is a plot showing a calibration curve of $H_2O_2$ at a non-glucose sensor.

The non-glucose sensor was in the presence of 50 µL of Phosphate Buffer Solution (PBS, pH=7.0) having varying concentrations of hydrogen peroxide (0-50 µM). Chronoamperometry (+4.0 V vs. Ag) was applied for 30 seconds at the sensor for each concentration of hydrogen peroxide. The current decreases with as the concentration of glucose increases. This suggests that the electrochemical measurement is of hydrogen peroxide being generated by the GOx reaction with glucose. FIG. 18 shows the linear relationship between the amperometric current and the hydrogen peroxide concentration with a sensitivity of $-1.2\times10^{-8}$ A$\mu$M$^{-1}$. Note that the sensitivity at the non-glucose sensor is higher than that of the glucose sensor, which is expected because the electrochemical surface area of the glucose sensor is lower than the sensor due to the surface area occupied with the GOx at the glucose sensor. This aligns well with the Randle-Sevgik equation, where the resulting current is proportionally related to the electrochemical surface area.

Salivary Glucose Diagnostic Device Architecture

A salivary glucose diagnostic device includes the glucose sensor and the non-glucose sensor. The salivary glucose diagnostic device can be embodied as a single chip point-of-care system that includes both sensors (as shown in FIG. 3) or a dual chip point-of-care system with each sensor included on a single chip (as shown in FIG. 2). Both the single and dual-chip systems can detect the glucose concentration indirectly in a small saliva sample e.g., a volume of the sample can be between 1 μL and 70 μL).

Salivary Glucose Diagnostic Device in Saliva

To test real human saliva, a collection method was established to ensure that all saliva samples are collected and processed in the same way to minimize sample variability during testing. The collection method includes (1) the user rinses their mouth with clean drinking water to allow regular saliva production over the period of a few minutes; (2) the user pools their saliva in the mouth and refrains from swallowing for approximately one minute; (3) once a sufficient saliva pool has accumulated, the user uses a swab to collect the pooled saliva; and (4) the saliva is extracted onto the salivary glucose diagnostic device using a syringe-type device. However, the user can directly expectorate the pooled saliva into a reservoir containing the salivary glucose diagnostic device. As another example, the collection of saliva can be by a swab. In a further example, the collection of saliva can be through collection of passive drool.

Glucose testing on real human saliva was carried out using chronoamperometry (+0.4 V vs. Ag for 30 seconds) at the salivary glucose diagnostic device to determine whether varying amounts of glucose will be detected in real world samples.

Figure 19:
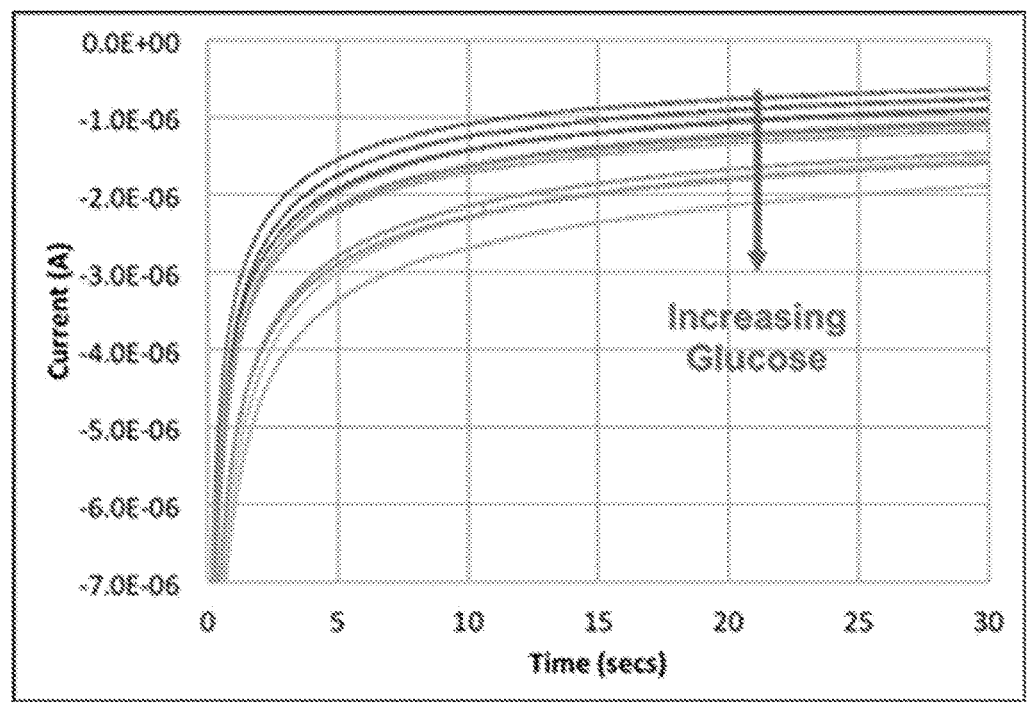
FIG. 19 is a plot showing chronoamperometry of a salivary glucose diagnostic device in real human saliva at varying concentrations of glucose.
Figure 20:
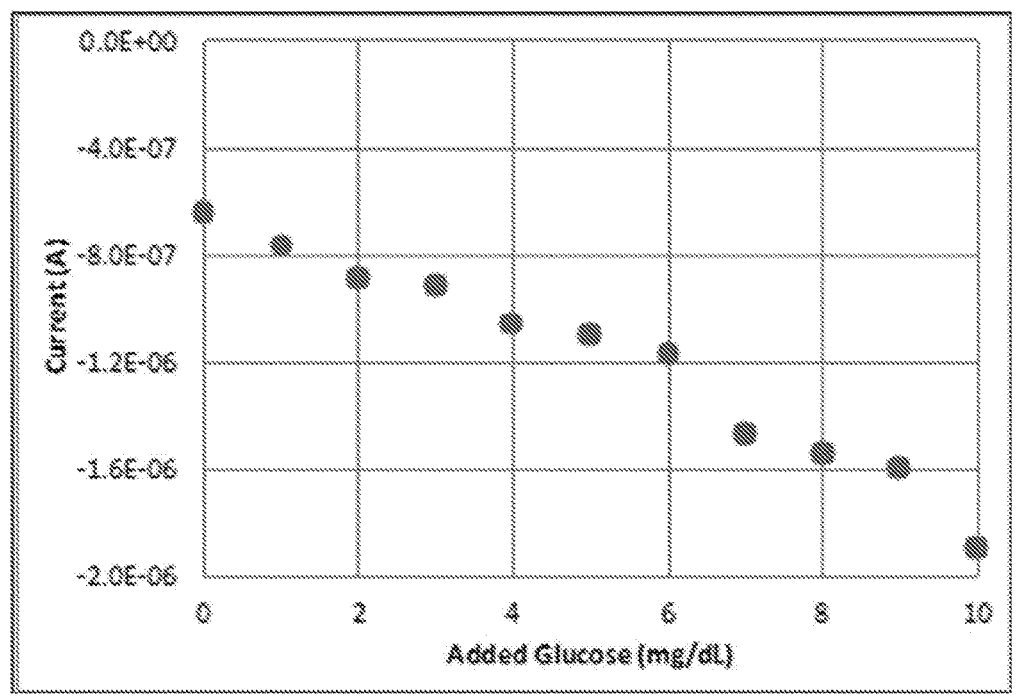
FIG. 20 is a plot showing amperometric current plotted against added glucose at the salivary glucose diagnostic device in the presence of real human saliva.

FIG. 19 shows the chronoamperogram of human saliva containing varying amounts of added glucose (0-10 mg/dL). The trend seems to correlate well with the experiment done in PBS, as the amperometric current decreases as the concentration of added glucose increases. FIG. 20 shows the amperometric current plotted against the added concentration of glucose. The figure shows a linear relationship with a sensitivity of $-1.2\times10^{-7}$ A mg$^{-1}$dL$^{-1}$. The senility of varying glucose in saliva is very similar to that of PBS, which indicates that there are little to no analytes within the saliva that can interfere with glucose detection by the salivary glucose diagnostic device. Thus, the calibration curves obtained in PBS can be applied to real human saliva samples.

Figure 21:
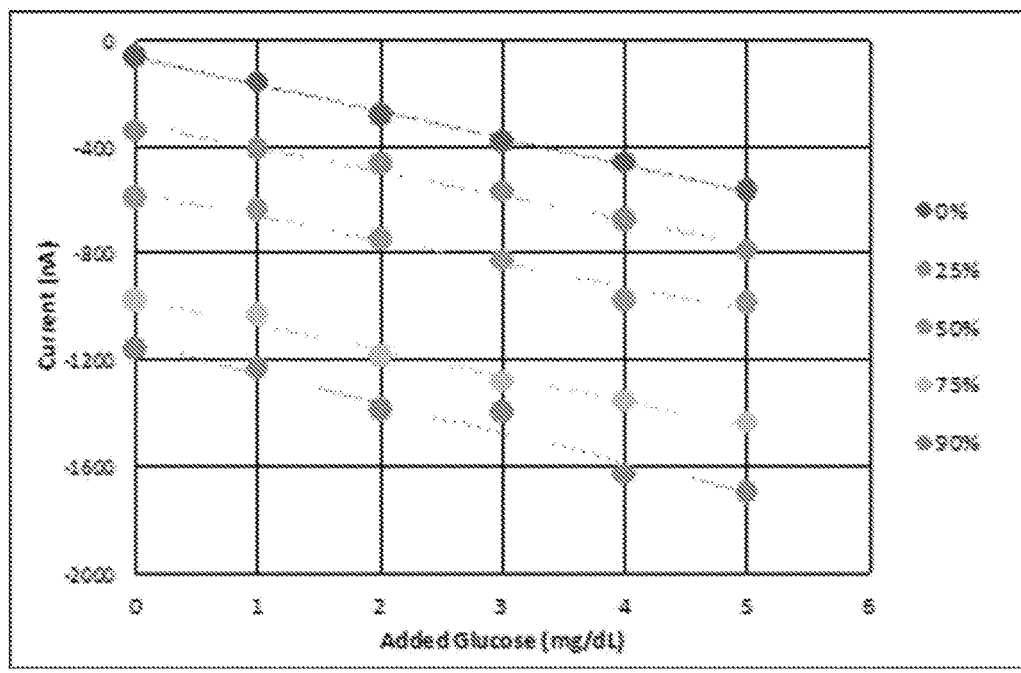
FIG. 21 is a plot showing the dilution effect on real human saliva samples at the salivary glucose diagnostic device at varying concentrations of added glucose.

To further test whether real human saliva itself does not contain interfering analytes, a dilution effect test was carried out. Saliva samples were diluted from 0% to 90% with PBS (pH 7.0) and were tested at varying concentrations of added glucose (0-5 mg/dL). FIG. 21 illustrates the amperometric current behavior in relation to the added concentration of glucose. The slopes at each dilution are the same, which suggests that saliva itself has little to no interfering analytes towards the detection of glucose.

As the next proof-of-concept, 11 saliva samples were obtained from 11 different volunteers, both diabetic and non-diabetic. The salivary glucose diagnostic device was tested alongside a commercially available glucose assay for comparison. The saliva samples were tested with the salivary glucose diagnostic device. First, the starting hydrogen peroxide concentration was determined using the non-glucose sensor. Then, the glucose sensor obtains the hydrogen peroxide product concentration given by the GOx reaction with glucose. The difference in hydrogen peroxide value and/or current can then be related to glucose concentration. Table 2 displays the results of the 11 saliva samples at the salivary glucose diagnostic device in comparison to the commercially available glucose assay.

TABLE 2

Results from the salivary glucose diagnostic device and the commercially available assay.

| Sample Name | Salivary Glucose Diagnostic Device (mg/dL) | Commercial Glucose Assay (mg/dL) | Absolute Value Difference (mg/dL) |
|---|---|---|---|
| SAL-018 | 0.95 | 0.75 | 0.21 |
| SAL-220-2 | 0.95 | 0.89 | 0.06 |
| SAL-220-5 | 0.69 | 0.70 | 0.01 |
| SAL-220-6 | 0.89 | 0.90 | 0.01 |
| SAL-220-7 | 0.50 | 0.87 | 0.37 |
| SAL-032 | 0.45 | 1.76 | 1.31 |
| SAL-214-1 | 0.31 | 0.52 | 0.21 |
| SAL-214-2 | 0.73 | 0.93 | 0.21 |
| SAL-220-4 | 0.62 | 1.05 | 0.44 |
| SAL-306-1 | 0.54 | 0.67 | 0.14 |
| SAL-306-2 | 0.50 | 0.54 | 0.04 |

The results between the salivary glucose diagnostic device and the commercially-available assay are very similar, which indicates that the salivary glucose diagnostic device can function as a novel point-of-care salivary glucose detection device.

From the above description, those skilled in the art will perceive improvements, changes and modifications. Such improvements, changes and modifications are within the skill of one in the art and are intended to be covered by the appended claims.

The invention claimed is:

1. A system comprising:
    a first sensor comprising:
        a first electrode;
        a base layer on the first electrode comprising carbon nanotubes to detect hydrogen peroxide in a saliva sample,
        wherein the hydrogen peroxide detected by the carbon nanotubes comprises the hydrogen peroxide in the saliva sample and hydrogen peroxide released as a reaction product from a glucose oxidase reaction in the presence of glucose;
        a middle layer on the base layer comprising chitosan; and
        a top layer on the middle layer to detect glucose in the saliva sample, comprising glucose oxidase and gold nanoparticles that binds to the chitosan of the middle layer; and
    a second sensor physically distinct from the first sensor and separated from the first sensor by a distance sufficient to ensure that the hydrogen peroxide released as the reaction product does not diffuse to the second sensor, the second sensor comprising a second electrode and at least one layer to detect the hydrogen peroxide in the saliva sample; and a detection unit device comprising a processor that executes instructions stored in a non-transitory memory to:

receive a first signal from the first sensor indicating the detected glucose and hydrogen peroxide;

receive a second signal from the second sensor indicating the detected hydrogen peroxide;

normalize the first signal and the second signal; and determine a concentration of the glucose in the saliva sample by taking the absolute value of the normalized second signal subtracted from the normalized first signal.

2. The system of claim 1, wherein the at least one layer of the second sensor comprises the base layer on the second electrode comprising carbon nanotubes to detect the hydrogen peroxide in the saliva sample.

3. The system of claim 1, whether the at least one layer of the second sensor further comprises the middle layer on the base layer comprising chitosan.

4. The system of claim 1, further comprising a third sensor, wherein the third sensor comprises:

a third electrode; and at least one third layer to detect at least one condition in the sample impacting detection at the first sensor and/or the second sensor.

5. The system of claim 1, wherein the processor is further to determine whether the patient associated with the saliva sample is diabetic, normal, or has a condition causing abnormal glucose concentration based on the absolute value of the second signal subtracted from the first signal.

* * * * *